(12) United States Patent
Yamashita

(10) Patent No.: US 7,105,323 B2
(45) Date of Patent: Sep. 12, 2006

(54) RECOMBINANT CAGE-LIKE PROTEIN, METHOD FOR PRODUCING THE SAME, PRECIOUS METAL-RECOMBINANT CAGE-LIKE PROTEIN COMPLEX, METHOD FOR PRODUCING THE SAME AND RECOMBINANT DNA

(75) Inventor: Ichiro Yamashita, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/229,240

(22) Filed: Sep. 16, 2005

(65) Prior Publication Data

US 2006/0024790 A1    Feb. 2, 2006

Related U.S. Application Data

(63) Continuation of application No. 10/142,838, filed on May 13, 2002, now Pat. No. 7,033,613.

(30) Foreign Application Priority Data

May 14, 2001    (JP)    .............................. 2001-142983

(51) Int. Cl.
  C12P 9/00    (2006.01)
  G01N 33/543    (2006.01)

(52) U.S. Cl. ...................... 435/131; 530/400; 530/350; 424/617; 424/600; 435/440; 426/328; 426/669; 514/2

(58) Field of Classification Search ................ 424/617, 424/600; 435/440, 131; 514/2; 530/350, 530/400; 426/328, 669
See application file for complete search history.

(56) References Cited

U.S. PATENT DOCUMENTS

| 4,847,199 A | 7/1989 | Snyder et al. |
| 5,358,722 A | 10/1994 | Monzyk |
| 6,713,173 B1 | 3/2004 | Mayes et al. |

FOREIGN PATENT DOCUMENTS

| EP | 0 881 691 A2 | 12/1998 |
| EP | 0 926 260 A2 | 6/1999 |
| EP | 1262489 A1 * | 12/2002 |
| JP | 8-083940 | 3/1996 |
| JP | 11-233752 | 8/1999 |
| WO | WO 91/02704 | 3/1991 |

OTHER PUBLICATIONS

D.J. Price et al.: "Ferritin"; The Journal of Biological Chemistry; vol. 258; No. 18; pp. 10873-10880; Sep. 1983.
James F. Hainfeld; "Uranium-loaded apoferritin with antibodies attached: Molecular design for uranium neutron-capture therapy"; Proc. Natl. Acad. Sci. USA; vol. 89, pp. 11064-11068; Nov. 1992.
J. Fleeming et al.; "Ferritin: Isolation of aluminum-ferritin complex from brain"; Proc. Natl. Acad. Sci. USA; vol. 84, pp. 7866-7870; Nov. 1987.
Trevor Douglas et al.; "Nanophase Cobalt Oxyhydroxide Mineral Synthesized within the Protein Cage of Ferritin"; 2000 American Chemical Society; vol. 39, No. 8, pp. 1828-1830; Mar. 2000.
Daniel Price et al.; "Ferritin: A zinc detoxicant and a zinc ion donor"; Proc. Natl. Acad. Sci. USA; vol. 79, pp. 3116-3119; May 1982.
Fiona C. Meldrum et al.; "Reconstitution of Manganese Oxide Cores in Horse Spleen and Recombinant Ferritins"; 1995 Elsevier Science Inc.; Journal of Inorganic Biochemistry; 58; pp. 59-68; 1995.
Hideyuki Yoshimura; "Two-Dimensional Crystals of Apoferritin"; Adv. Biophys.; vol. 34, pp. 93-107; 1997.
Shigeki Takeda et al.; "Cloning, expression and characterization of horse L-ferritin in *Escherichia coli*"; Elsevier Science Publishers B.V.; Biochimica et Biophysica Acta; 1174; pp. 218-220; 1993.
P. Hempstead et al.; "Comparision of the Three-dimensional Structures of Recombinant Human H and Horse L. Ferritins at High Resolution"; Journal of Molecular Biology, vol. 268, No. 2; 1997; pp. 424-448.
D. Boyd et al.; "Structural and Functional Relationships of Human Ferritin H and L Chains Deduced from Complementary DNA Clones"; Journal of Biological Chemistry; vol. 260, No. 21; 1985; pp. 11755-11761.
Douglas, T. et al.; (2000) "Nanophase cobalt oxyhydroxide mineral synthesized within the protein cage of ferritin"; Inorg Chem. vol. 39; pp. 1828-1830.
Frey, R. T. et al. (1995); "Iron in Biology: study of the Iron content in Ferritin, the Iron-storage protein"; pp. 1-10.
Mackie, P. et al.; "Characterization of the Manganese Core of Reconstituted Ferritin by Xray Absorption Spectroscopy"; America Chemical Society; vol. 115, No. 18, pp. 8471-8472; May 1993.
Levi, S. et al.; (1996) Evidence that residues exposed on the three-fold channels have active roles in the mechanism of ferritin iron incorporation. Biochem. J. vol. 317, pp. 467-473.
Gupta, S. et al.; (2002) Proteomics anaylsis of carbon-starved Mycobacterium smegmatis:induction of Dps-like protein. Protein. Eng. vol. 15, pp. 503-511.
Voss-Andreae, J. (2005) Protein Sculptures:life's building blocks inspire art. Leonardo; vol. 38; pp. 41-45.

* cited by examiner

Primary Examiner—Jon Weber
Assistant Examiner—Samuel Wei Liu
(74) Attorney, Agent, or Firm—Harness, Dickey & Pierce, P.L.C.

(57) ABSTRACT

The present invention relates to a precious metal-recombinant apoferritin complex produced by recombination technique, wherein the precious metal is gold (Au) or platinum (Pt), and wherein the residues of glutamic acid and aspartic acid in a channel of apoferritin complex are substituted with small polar amino acid residues or/and noncharged amino acid residues, e.g., serine, or/and with basic amino acid residues, e.g., lysine. The substitution prevents a repulsive force due to electrostatic interaction between a metal ion, e.g., $(AuCl_4)^-$ that has a negative charge and a negative amino acid residue of the apoferritin, and facilitates the capture of $(AuCl_4)^-$ into holding portion in the channel of said metal-recombinant apoferritin complex. The captured $(AuCl_4)^-$ is subsequently reduced to Au, and thus the gold-recombinant apoferritin complex is produced.

24 Claims, 9 Drawing Sheets

(a)

(b)

(c)

(a)

(b)

(c)

SEQUENCE LISTING

<160> NUMBER OF SEQ ID NOS: 2

<210> SEQ ID NO 1
<211> LENGTH: 504
<212> TYPE: DNA
<213> ORGANISM: Artificial Sequence
<220> FEATURE:
<223> OTHER INFORMATION: Description of Artificial Sequence:Recombinant
      DNA of Liver Apoferritin of Equus cebellus

<400> SEQUENCE: 1

```
tattctactg aagtggaggc cgccgtcaac cgcctggtca acctgtacct gcgggcctcc     60
tacacctacc tctctctggg cttctatttc gaccgcgacg atgtggctct ggagggcgta    120
tgccacttct tccgctgctt ggcggagaag aagcgcaagg gtgccaagtg cctcttgaag    180
atgcaaaacc agcgcggcgg ccgcgccctc ttccagagct tgtccaagcc gtcccaggat    240
gaatggggta caccccggga tgccatgaaa gccgccattg tcctggagaa gagcctgaac    300
caggcccttt tggatctgca tgccctgggt tctgcccagg cagaccccca tctctgtagc    360
ttcttgtcta gccacttcct agacgaggag gtgaaactca tcaagaagat gggcgaccat    420
ctgaccaaca tccagaggct cgttggctcc caagctgggc tgggcgagta tctctttgaa    480
aggctcactc tcaagcacga ctaa                                            504
```

<210> SEQ ID NO 2
<211> LENGTH: 167
<212> TYPE: PRT
<213> ORGANISM: Artificial Sequence
<220> FEATURE:
<223> OTHER INFORMATION: Description of Artificial Sequence:Recombinant
      Liver Apoferritin of Equus cebellus
<220> FEATURE:
<221> NAME/KEY: MUTAGEN
<222> LOCATION: (46)
<220> FEATURE:
<221> NAME/KEY: MUTAGEN
<222> LOCATION: (50)
<220> FEATURE:
<221> NAME/KEY: MUTAGEN
<222> LOCATION: (53)
<220> FEATURE:
<221> NAME/KEY: MUTAGEN
<222> LOCATION: (56)
<220> FEATURE:
<221> NAME/KEY: MUTAGEN
<222> LOCATION: (57)
<220> FEATURE:
<221> NAME/KEY: MUTAGEN
<222> LOCATION: (120)
<220> FEATURE:
<221> NAME/KEY: MUTAGEN
<222> LOCATION: (123)

<400> SEQUENCE: 2

```
Tyr Ser Thr Glu Val Glu Ala Ala Val Asn Arg Leu Val Asn Leu Tyr
 1               5                  10                  15

Leu Arg Ala Ser Tyr Thr Tyr Leu Ser Leu Gly Phe Tyr Phe Asp Arg
                20                  25                  30

Asp Asp Val Ala Leu Glu Gly Val Cys His Phe Phe Arg Cys Leu Ala
            35                  40                  45

Glu Lys Lys Arg Lys Gly Ala Lys Cys Leu Leu Lys Met Gln Asn Gln
        50                  55                  60

Arg Gly Gly Arg Ala Leu Phe Gln Asp Leu Gln Lys Pro Ser Gln Asp
65                  70                  75                  80
```

```
Glu Trp Gly Thr Thr Pro Asp Ala Met Lys Ala Ala Ile Val Leu Glu
                85              90              95

Lys Ser Leu Asn Gln Ala Leu Leu Asp Leu His Ala Leu Gly Ser Ala
            100             105             110

Gln Ala Asp Pro His Leu Cys Ser Phe Leu Ser Ser His Phe Leu Asp
        115             120             125

Glu Glu Val Lys Leu Ile Lys Lys Met Gly Asp His Leu Thr Asn Ile
        130             135             140

Gln Arg Leu Val Gly Ser Gln Ala Gly Leu Gly Glu Tyr Leu Phe Glu
145             150             155             160

Arg Leu Thr Leu Lys His Asp
                165
```

RECOMBINANT CAGE-LIKE PROTEIN, METHOD FOR PRODUCING THE SAME, PRECIOUS METAL-RECOMBINANT CAGE-LIKE PROTEIN COMPLEX, METHOD FOR PRODUCING THE SAME AND RECOMBINANT DNA

This application is a continuation of U.S. patent application Ser. No. 10/142,838 filed on May 13, 2002, now U.S. Pat. No. 7,033,613, issued Apr. 25, 2006. This application also claims the benefit of Japanese Patent Application No. 2001-142983 filed May 14, 2001. The disclosure(s) of the above application(s) are incorporated herein by reference.

BACKGROUND OF THE INVENTION

The present invention relates to a precious metal-recombinant apoferritin complex produced with a gene recombination technique and a method for producing the same, and techniques related thereto.

In recent years, in-depth research on bioelectronics, which is a combination of biotechnology and electronics, has been conducted, and some products such as biosensors employing proteins such as enzymes already have been put to practical use.

As one attempt to apply biotechnology to other fields, there is research in which fine particles made of metal or metal compounds are incorporated into apoferritin, which is a protein having the function of holding metal compounds, to produce the fine particles having uniform sizes of nm order. Research to introduce various metals or metal compounds suitable to the application of the fine particles into apoferritin has been under way.

Hereinafter, apoferritin will be described. Apoferritin is a protein that exists widely in the biological world and has the role of regulating the amount of iron, which is an essential trace element in living organisms. A complex of iron or an iron compound of apoferritin is called ferritin. If iron is present in an amount more than necessary, it is harmful to living organisms, so that excessive iron is stored in the form of ferritin. The ferritin releases an iron ion as necessary and is converted back to apoferritin.

FIG. 1 is a schematic view showing the structure of ferritin (iron-apoferritin complex). As shown in FIG. 1, ferritin is a spherical protein having a molecular weight of about 460,000 in which 24 monomer subunits constituting one polypeptide chain are assembled by non-covalent bonds, has a diameter of about 12 nm, and exhibits higher thermal stability and higher pH stability than those of common proteins. A hollow holding portion 4 having a diameter of about 6 nm is present in the center of this spherical protein (outer shell 2), and the holding portion 4 is connected to the outside via a channel 3. For example, when incorporating a bivalent iron ion into ferritin, the iron ion enters it through the channel 3 and is oxidized in a site called "ferrooxidase center" in a subunit in a portion thereof, and then reaches the holding portion 4 and is concentrated in a negative load region on the inner surface of the holding portion 4. Then, 3000 to 4000 iron atoms assemble and are held in the holding portion 4 in the form of ferrihydrite ($5Fe_2O_3 \cdot 9H_2O$) crystal.

In this specification, a fine particle including a metal atom held in the holding portion is referred to as a "core". The diameter of the core 1 shown in FIG. 1 is substantially equal to the diameter of the holding portion 4, which is about 6 nm.

The core 1 can be removed by a comparatively simple chemical operation, and the particle constituted only by the outer shell 2 without the core 1 is called apoferritin. Using apoferritin, an apoferritin-fine particle complex in which a metal or a metal compound other than iron is supported artificially has been produced.

To date, it has been reported that metals such as manganese (P. Mackle, 1993, J. Amer. Chem. Soc. 115,8471–8472; F. C. Meldrum et al., 1995, J. Inorg. Biochem. 58, 59–68), uranium (J. F. Hainfeld, 1992, Proc. Natl. Acad. Sci. USA 89,11064–11068), beryllium (D. J. Price, 1983, J. Biol. Chem. 258, 10873–10880), aluminum (J. Fleming, 1987, Proc. Natl. Acad. Sci. USA, 84, 7866–7870), zinc (D. Price and J. G. Joshi, Proc. Natl. Acad. Sci. USA, 1982, 79, 3116–3119), and cobalt (T. Douglas and V. T. Stark, Inorg. Chem., 39, 2000, 1828–1830) or metal compounds are introduced into apoferritin. The diameter of the core 1 made of these metals or metal compounds is also substantially equal to the diameter of the holding portion 4 of the apoferritin, which is about 6 nm.

The process for forming the core 1 including an iron atom in ferritin in the natural world proceeds generally in the following manner.

An amino acid having a negative charge at pH 7–8 is exposed onto the surface of the channel 3 (see FIG. 1) for connecting the outside and the inside of the ferritin particle, and a $Fe^{2+}$ ion having a positive charge is captured by the channel 3 by electrostatic interaction. The channels 3 are present in the number of 8 per apoferritin.

As on the inner surface of the channel 3, a large number of glutamic acid residues, which are amino acid residues having a negative charge at pH 7–8, are exposed onto the inner surface of the holding portion 4 of the ferritin, and $Fe^{2+}$ ions captured from the channel 3 are oxidized at the ferroxidase center and led to further inside of the holding portion 4. Then, the iron ions are concentrated by electrostatic interaction and nucleus formation of a ferrihydrite ($5Fe_2O_3 \cdot 9H_2O$) crystal occurs.

Thereafter, iron ions that are sequentially captured are attached to the nucleus of this crystal, so that the nucleus made of iron oxide is grown and thus the core 1 having a diameter of 6 nm is formed in the holding portion 4. The capture of iron ions and the formation of the nucleus made of iron oxide are performed generally in the manner as described above.

Next, an operation for introducing iron to apoferritin will be described below.

First, a HEPES buffer solution, an apoferritin solution, and an ammonium iron sulfate ($Fe(NH_4)_2(SO_4)_2$) solution are mixed in this order to prepare a ferritin solution. In this ferritin solution, the final concentrations of the HEPES buffer solution, apoferritin and ammonium iron sulfate are 100 mmol/L (pH 7.0), 0.5 mg/mL, and 5 mmol/L, respectively. All the operations for preparing ferritin are performed at room temperature and stirring is performed with a stirrer.

Next, in order to complete a reaction for capturing iron ions into apoferritin and an oxidation reaction of the captured irons, the ferritin solution is allowed to stand over night. This operation introduces iron oxides having uniform sizes into the holding portion of apoferritin, so that ferritin (a complex of apoferritin and a fine particle) is produced;

Next, the ferritin solution is placed in a container, and centrifuged at 3,000 rpm with a centrifugal separator for 15 to 30 min to remove a precipitate. Then, the resultant supernatant obtained after the precipitate is removed is centrifuged further at 10,000 rpm for 30 min so as to precipitate an unwanted ferritin aggregate and remove it. At this point, ferritin is present in the supernatant in the form of a dispersion.

Next, as the solvent of this supernatant, the 100 mmol/L HEPES buffer solution of pH 7.0 is replaced by a 150 mmol/L NaCl solution by dialysis to prepare a new ferritin solution. Here, the pH does not necessarily have to be adjusted.

Then, this ferritin solution is concentrated to an arbitrary concentration between 1 and 10 mg/mL, and then $CdSO_4$ is added to this solution such that the final concentration thereof becomes 10 mmol/L to aggregate the ferritin.

Next, the ferritin solution is centrifuged at 3,000 rpm for 20 min to precipitate a ferritin aggregate in the solution. Thereafter, the buffer component in the solution is replaced by a 10–50 mmol/L Tris buffer solution of pH 8.0 containing 150 mmol/L NaCl by dialysis.

Next, the ferritin solution is concentrated and then is filtrated by gel filtration column to remove an aggregate of ferritin particles, so that discrete ferritin including iron oxide can be obtained.

The mechanism for capturing iron ions into ferritin and a method for preparing ferritin including iron oxide have been described above. Since all the other metal ions that have been reported so far to be introduced are positive ions, it is believed that the capture of these metal ions to apoferritin substantially in the same mechanism as in the case of iron ions. Therefore, the other ions basically can be introduced into apoferritin substantially in the same operations as in the case of iron ions.

Regarding apoferritin, the size of a particle that can be held slightly varies with the type of the organism from which it is derived. Furthermore, there are spherical proteins that have similar structures to that of apoferritin and can hold inorganic particles inside. Examples thereof include Listeria ferritin derived from Listeria monocytogenes and Dps protein. There are proteins that are not spherical but can hold an inorganic particle similarly to ferritin, such as outer shell proteins of virus such as CCMV.

In the specification of the present application, proteins that can hold inorganic particles inside such as spherical proteins, outer shell proteins of virus are referred to as "cage-like proteins".

These cage-like proteins can hold inorganic particles including iron.

Thus, ferritin holding a metal ion such as iron can be produced in the above-described method. However, since the inner surface of the channel 3 of apoferritin and ferritin is positively charged as a whole, it is difficult to capture ions having the same negative charge into apoferritin.

On the other hand, gold, platinum or the like cannot be ionized alone in an aqueous solution, and only can be present as complex ions in an aqueous solution. Therefore, they are often used in the form of negative ions of chloroauric acid ions $(AuCl_4)^-$ or $(PtCl_4)^{2-}$. Consequently, it was difficult to capture precious metal atoms such as gold or platinum into apoferritin in the prior art.

SUMMARY OF THE INVENTION

Therefore, with the foregoing in mind, it is an object of the present invention to introduce precious metal atoms such as gold into a cage-like protein such as apoferritin by modifying the inner structure of a cage-like protein such as apoferritin, and thus to form precious metal particles applicable to various microstructures.

A recombinant cage-like protein of the present invention is produced by a gene recombination technique and includes a holding portion that is present in an internal portion of the recombinant cage-like protein and can hold a precious metal particle; and a tunnel-like channel for connecting the holding portion and an outside of the recombinant cage-like protein.

Thus, a precious metal particle having a uniform size of nanometer order can be formed in the holding portion of the recombinant cage-like protein, so that minute dot bodies made of a precious metal having excellent chemical stability by, for example, arranging precious metal-recombinant cage-like protein complexes on a substrate and removing the protein portion. These dot bodies can be utilized, for example, in a process for producing a semiconductor.

The recombinant cage-like protein is apoferritin, so that a precious metal particle having a size of the nanometer order can be produced efficiently.

The precious metal particle is gold or platinum, so that the formation of the dot bodies can be facilitated. The produced fine particles can be applied to single-electron transistors or the like.

The recombinant cage-like protein includes a first neutral amino acid that has a smaller molecular size than that of glutamic acid (Glu) and that of aspartic acid (Asp) in positions on an inner surface of the channel in which a first glutamic acid and a first aspartic acid are to be present, so that a repulsive force due to electrostatic interaction between precious metal complex ions having a negative charge and the channel is prevented from occurring. As a result, the precious metal complex ions can be captured by the channel.

The first neutral amino acid is selected from the group consisting of serine, alanine, and glycine, so that precious metal complex ions can be captured by the channel without breaking the stereostructure of the recombinant cage-like protein.

The recombinant cage-like protein further includes a basic amino acid or a second neutral amino acid in a position in the inner surface of the holding portion in which a second glutamic acid is to be present, so that a repulsive force due to electrostatic interaction between precious metal complex ions having a negative charge and the holding portion is prevented from occurring. In particular, when a basic amino acid is provided in a position in which the second glutamic acid is to be present, precious metal complex ions having negative charges are captured because of positive charges of this basic amino acid, so that the precious metal complex ions can be captured in a high concentration by the holding portion.

The basic amino acid or the second neutral amino acid is selected from the group consisting of arginine, lysine, and alanine, so that precious metal complex ions can be captured by the holding portion without breaking the stereostructure of the recombinant cage-like protein.

At least one cysteine substituted for an amino acid is present on the inner surface of the holding portion, so that precious metal complex ions captured by the holding portion can be reduced effectively, and precious metal particles can be precipitated.

The recombinant cage-like protein includes a substance having smaller reduction function than that of cysteine in a position on the outer surface of the recombinant cage-like protein in which cysteine is to be present, so that the precious metal complex ions are prevented from being reduced on the outer surface of the recombinant cage-like protein. As a result, the precious metal particles are prevented from being precipitated on the outer surface of the recombinant cage-like protein, so that the yield of the precious metal-recombinant cage-like protein that holds a precious metal particle in the holding portion can be increased.

A precious metal-recombinant cage-like protein complex of the present invention includes a holding portion that can hold a precious metal particle and a tunnel-like channel for connecting the holding portion and the outside of the recombinant cage-like protein.

Thus, minute dot bodies made of the precious metal can be formed on a substrate by, for example, arranging the precious metal-recombinant cage-like protein complexes on a substrate and removing the protein portion. These dot bodies can be utilized, for example, in a process for producing a semiconductor.

The recombinant cage-like protein may be apoferritin.

The cage-like protein may hold a gold or platinum particle on the outer surface thereof The precious metal-recombinant cage-like protein complex includes a first neutral amino acid that has a smaller molecular size than that of glutamic acid and that of aspartic acid in positions on the inner surface of the channel in which a first glutamic acid and a first aspartic acid are to be present, so that a repulsive force due to electrostatic interaction between precious metal complex ions having a negative charge and the channel is prevented from occurring. As a result, the precious metal-recombinant cage-like protein complex can be produced efficiently.

The first neutral amino acid can be selected from the group consisting of serine, alanine and glycine, so that the precious metal-recombinant cage-like protein complex can be formed without the stereostructure.

The precious metal-recombinant cage-like protein complex further includes a basic amino acid or a second neutral amino acid in a position in the inner surface of the holding portion in which a second glutamic acid is to be present, so that a repulsive force due to electrostatic interaction between precious metal complex ions having a negative charge and the holding portion is prevented from occurring. As a result, the precious metal-recombinant cage-like protein complex can be produced efficiently.

The basic amino acid or the second neutral amino acid is selected from the group consisting of arginine, lysine, and alanine, so that the precious metal particles can be held without breaking the stereostructure.

At least one cysteine substituted for an amino acid is present on the inner surface of the holding portion, so that the precious metal--recombinant cage-like protein complex can be formed easily in a solution containing precious metal ions.

A recombinant DNA of the present invention encodes an amino acid sequence of a recombinant cage-like protein including a holding portion that can hold a precious metal particle and a tunnel-like channel for connecting the holding portion and the outside of the recombinant cage-like protein.

This recombinant DNA makes it possible to mass-produce the recombinant cage-like protein using a protein engineering technique.

The recombinant cage-like protein may be apoferritin.

The precious metal particle may be gold or platinum.

The recombinant DNA includes a first neutral amino acid that has a smaller molecular size than that of glutamic acid and that of aspartic acid in positions on the inner surface of the channel in which a first glutamic acid and a first aspartic acid are to be present, so that the recombinant protein can be obtained easily.

The first neutral amino acid is selected from the group consisting of serine, alanine and glycine, so that a large amount of the recombinant cage-like protein to form precious metal particles efficiently in the holding portion can be obtained.

The recombinant DNA further includes a basic amino acid or a second neutral amino acid in a position on the inner surface of the holding portion in which a second glutamic acid is to be present, so that a large amount of homogeneous recombinant cage-like protein to form precious metal particles efficiently in the holding portion can be obtained.

The basic amino acid or the second neutral amino acid is selected from the group consisting of arginine, lysine, and alanine, so that recombinant cage-like protein that can hold precious metal particles efficiently can be obtained easily.

At least one cysteine substituted for an amino acid is present on the inner surface of the holding portion, so that recombinant cage-like protein that can hold precious metal particles more efficiently can be obtained easily.

A method for producing a recombinant cage-like protein of the present invention includes the step (a) of substituting a first glutamic acid and a first aspartic acid that are positioned on the inner surface of a channel with a first neutral amino acid having a smaller molecular size than that of glutamic acid and that of aspartic acid.

This method makes it possible to easily produce the recombinant cage-like protein that can capture precious metal particles into the channel efficiently.

The cage-like protein may be apoferritin.

In the step (a), the first neutral amino acid is selected from the group consisting of serine, alanine, and glycine, so that it is possible to produce a recombinant cage-like protein that can capture precious metal complex ions into the channel without breaking the stereostructure of the recombinant cage-like protein.

The method for producing a recombinant cage-like protein further includes the step (b) of substituting a second glutamic acid present on the inner surface of the holding portion that is inside the recombinant cage-like protein with a basic amino acid or a second neutral amino acid, so that the recombinant cage-like protein that can capture precious metal particles into the holding portion efficiently can be produced easily.

In the step (b), the basic amino acid or the second neutral amino acid is selected from the group consisting of arginine, lysine and alanine, so that precious metal complex ions can be captured into the holding portion without breaking the stereostructure of the recombinant cage-like protein.

The method for producing a recombinant cage-like protein further includes the step (c) of substituting at least one amino acid positioned on the inner surface of the holding portion with cysteine, so that a recombinant cage-like protein that allows precious metal complex ions captured into the holding portion to be reduced effectively to precipitate precious metal particles. When the precious metal complex ions are reduced, the molecular size is decreased, so that the capture of the precious metal complex ions into the holding portion can be promoted.

The method for producing a recombinant cage-like protein further includes the step (d) of replacing at least one cysteine positioned on the outer surface of the recombinant cage-like protein by a substance having a smaller reduction function than that of cysteine, so that a recombinant cage-like protein in which the reduction of the precious metal complex ions on the outer surface is suppressed can be produced.

A method for producing a precious metal-recombinant cage-like protein complex includes the steps: (a) mixing a precious metal complex ion solution and a recombinant cage-like protein solution to form a precious metal-recombinant cage-like protein complex, and (b) passing a solution containing the precious metal-recombinant cage-like protein complex prepared in the step (a) through a gel filtration column to purify the precious metal-recombinant cage-like protein complex.

This method makes it possible to fractionate the recombinant cage-like protein holding precious metal on the outer surface, the recombinant cage-like protein including the precious metal, and a side reaction product or the like from each other by the size, so that a desired purified precious metal-recombinant cage-like protein complex can be selected.

The precious metal in the step (a) is gold or platinum, so that as described above, the dot bodies made of gold or platinum to be utilized in, for example, a production process of a semiconductor device or the like can be formed, and in this process, the reduction process of the dot bodies, which was conventionally necessary, can be eliminated.

DETAILED DESCRIPTION OF THE INVENTION

First Embodiment

A first embodiment of the present invention will be described below.

Production of Recombinant Apoferritin

The inventors of the present invention considered the following two aspects to be primary detriments to the introduction of gold (Au) atoms into apoferritin.

Figure 1:
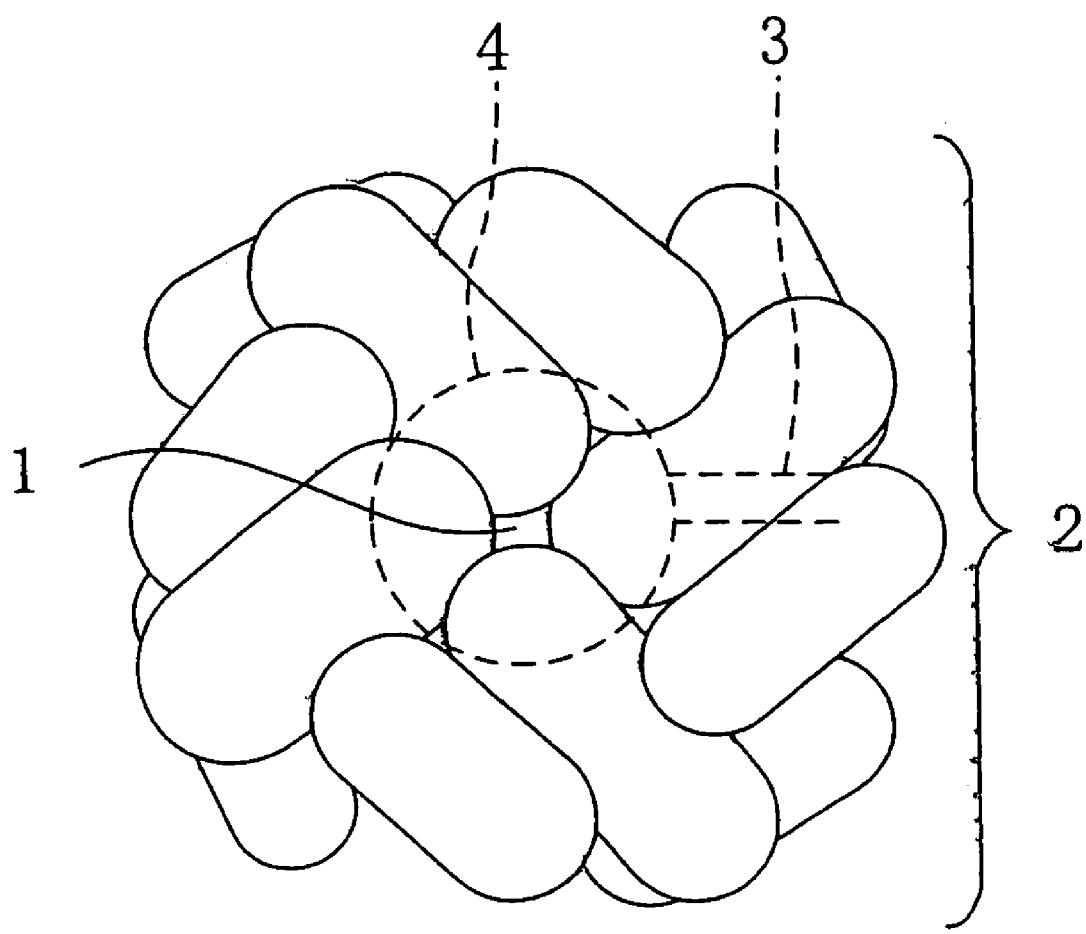
FIG. 1 is a schematic view showing the structure of ferritin.

One is electrostatic interaction between a chloroauric acid ion $(AuCl_4)^-$ and apoferritin. The amino acids that have negative charges, such as glutamic acid or aspartic acid, are exposed onto the inner surface of the channel 3 and the inner surface of the holding portion 4 of ferritin (apoferritin-iron complex) shown in FIG. 1. The capture of $(AuCl_4)^-$, which is a negative ion, into apoferritin is inhibited by an electrostatic interaction with these amino acids having negative ions.

Another detriment is that the size of $(AuCl_4)^-$ is larger than that of an iron ion. For this reason, unless the size of the channel 3 of the apoferritin is increased, it is physically difficult to capture $(AuCl_4)^-$ into the channel 3.

In order to solve these problems, the inventors modified apoferritin with a technique of gene recombination in the following manner. Hereinafter, in this specification, "recombinant apoferritin" refers to apoferritin to which a variation is introduced with a gene recombination technique. When a site of an amino acid residue is specified in this specification, it means, unless otherwise, a site of apoferritin derived from equine liver to which no variation is introduced. Since apoferritin is constituted with 24 monomer subunits, "the amino acid sequence of apoferritin" means the amino acid sequence of the monomer subunits.

The gene sequence encoding apoferritin derived from equine liver and the amino acid sequence of apoferritin are known, and the stereostructure thereof has been clarified. The monomer of apoferritin is constituted with 175 amino acid residues. Among these, the $128^{th}$ amino acid residue of aspartic acid (Asp) and the $131^{st}$ amino acid residue of glutamic acid (Glu) are both positioned on the inner surface of the channel 3, and the $58^{th}$, $61^{st}$ and $64^{th}$ amino acid residues of glutamic acids are all positioned on the inner surface of the holding portion 4. The first to eighth amino acid residues are deleted by in vivo processing.

Next, the electrostatic interaction in apoferritin will be described.

As described above, aspartic acid and glutamic acid having negative charges are located on the inner surfaces of the holding portion 4 and the channel 3 of apoferritin in a neutral solution, so that the potential Vin of the entire inner surface of the apoferritin is lower than the potential Vout of the outside of the apoferritin. More specifically, the difference $\Delta V$ in the potential between the inside and the outside of the apoferritin defined as $\Delta V = Vin - Vout$ is $\Delta V < 0$ (mV).

Here, since $(AuCl_4)^-$ has a negative charge, it is known that the relationship between Cin, Cout and $\Delta V$ is expressed by the following equation (1), where Cin is the concentration of $(AuCl4)^-$ inside the apoferritin, and Cout is the concentration of $(AuCl_4)^-$ in the solution.

$$Cout/Cin = e^{-\Delta V/kT} \quad (1)$$

where e is a natural logarithm, k is Boltzmann logarithm, and T is an absolute temperature. This equation indicates that when the temperature is constant, the $(AuCl_4)^-$ concentration inside the apoferritin can be increased exponentially by increasing $\Delta V$. For example, when $\Delta V$ is a positive value and $\Delta V$ is increased by a factor of 4, Cout/Cin is about 80.

On the other hand, the reduction reaction of $(AuCl_4)^- \rightarrow$ Au in the inner surface of the apoferritin is accelerated as the concentration inside the apoferritin increases.

Considering the above conditions, the inventors of the present invention concluded that it is necessary that Cin is at least three times larger than Cout in order to produce gold particles efficiently in the holding portion 4 of the apoferritin in a solution. $\Delta V$ that satisfies this condition at room temperature is about 25 (mV) or more. In particular, in order to produce gold particles in the holding portion 4 at a sufficient speed, it seems to be preferable that $\Delta V$ is about 100 (mV) or more.

Herein, $\Delta V$ can be obtained by adding all the charges of the bases present on the inner surface of the apoferritin, taking the position into consideration. For example, three of the glutamic acids positioned in the holding portion 4 is substituted with lysine (Lys) in an apoferritin monomer, so that $\Delta V$ in the apoferritin is calculated to be about 200 mV This is believed to be a sufficient potential difference to produce gold particles in the holding portion 4 of the apoferritin.

The inventors of the present invention produced a recombinant apoferritin as follows that can hold gold particles, based on the above calculations.

Figure 2:
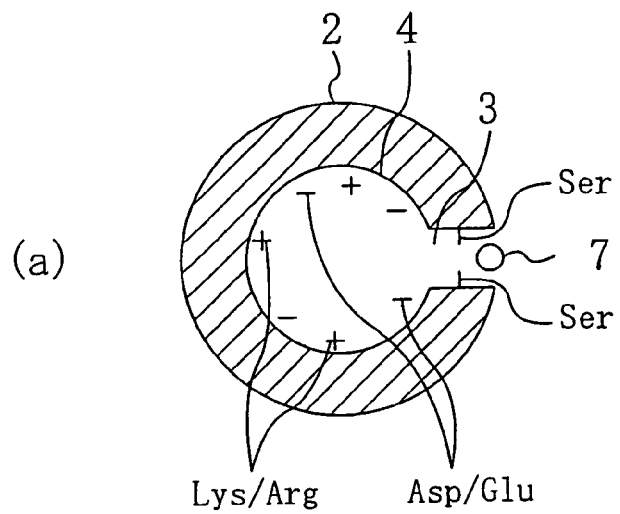
FIGS. 2a to 2c are schematic cross-sectional views of recombinant apoferritin according to a first embodiment of the present invention.
Figure 2:
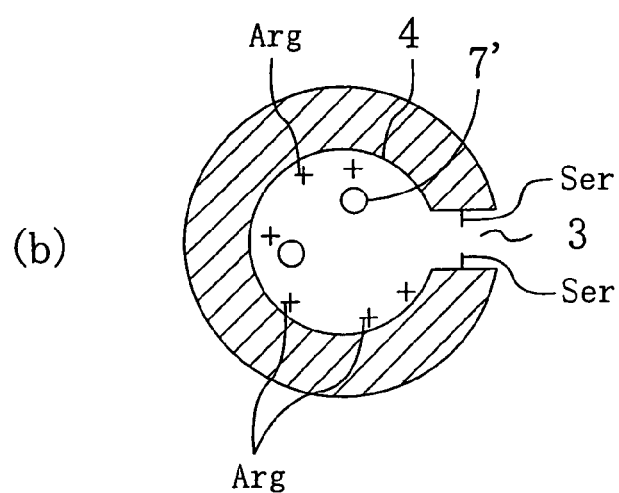
Figure 2:
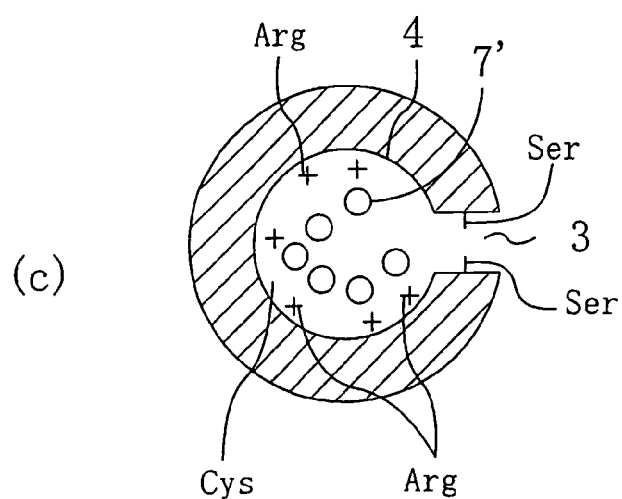

FIGS. 2A to 2C are schematic views showing the structure of a recombinant apoferritin produced based on the above findings.

First, FIG. 2A shows apoferritin derived from equine liver (hereinafter, referred to as "apoferritin") in which the $128^{th}$ amino acid of aspartic acid (Asp) and the 131st amino acid of glutamic acid (Glu) are substituted with serine (Ser). Even if aspartic acid or glutamic acid is substituted with serine, the stereostructure of the apoferritin can be maintained. The first to the eight amino acids in the apoferritin are projected from the outer surface of the apoferritin, and may cause a problem in producing a higher order structure such as two-dimensional crystallization, so that they are deleted. This recombinant apoferritin is expressed as "fer-8-ser" in the following.

The substitution of aspartic acid and glutamic acid having negative charges present on the inner surface of the channel 3 with serine having no charge eliminates electrostatic repulsion, which makes it easier to capture $(AuCl_4)^-$ (7 in FIG. 2A) having a negative charge into the channel 3. Furthermore, since the serine residue has a smaller size than that of the aspartic acid residue or the glutamic acid residue, so that the physical detriment to the capture of $(AuCl_4)^-$ into the channel is smaller.

Next, FIG. 2B shows a recombinant apoferritin in which the $58^{th}$, $61^{st}$ and $64^{th}$ amino acids of glutamic acids in the amino acid sequence of fer-8-Ser are each substituted with arginine (Arg). This recombinant apoferritin is expressed as "fer-8-Ser-Arg" in the following.

The substitution of the $58^{th}$, $61^{st}$ and $64^{th}$ amino acids of glutamic acids present on the inner surface of the holding portion 4 of the apoferritin with arginine having a positive charge makes it possible to guide $(AuCl_4)^-$ captured by the channel 3 to the holding portion 4 of the apoferritin. In this case, even if the glutamic acid is substituted with arginine, the stereostructure of the apoferritin can be maintained. The $(AuCl_4)^-$ 7 guided to the holding portion 4 are sequentially reduced to gold (Au) atoms 7'. As the amino acid that is substituted with the $58^{th}$, $61^{st}$ and $64^{th}$ amino acids of glutamic acids, any amino acid that has no negative charge can be used, and Lys, which is a basic amino acid, Ala, which is a nonpolar amino acid, and a neutral amino acid can be used.

Next, FIG. 2C shows a recombinant apoferritin in which the $54^{th}$ amino acid of glutamic acid and the $65^{th}$ amino acid of arginine in the amino acid sequence of fer-8-Ser-Arg are substituted with cysteine (Cys). This recombinant apoferritin is expressed as "fer-8-Ser-Arg-Cys" in the following.

The $54^{th}$ amino acid of glutamic acid and the $65^{th}$ amino acid of arginine in the amino acid sequence of fer-8-Ser-Arg are present on the inner surface of the holding portion 4 of apoferritin, so that the substitution of these amino acids with cysteine makes it possible to reduce the $(AuCl_4)^-$ 7 captured by the holding portion 4 so that gold fine particles can be precipitated. Thus, the core 1 made of gold can be formed in the holding portion 4 by the operations described later.

To produce the above-described recombinant apoferritin, a known gene recombination technique and a method for expressing a protein are used in the manner as described below.

First, a DNA fragment that encodes the amino acid sequence of apoferritin is cut out with a suitable restriction enzyme from a plasmid Takeda99224 (see S. Takeda et al. Biochim. Biophys. Acta., 1174,218–220, 1993) produced by Takeda et al. in which DNA of apoferritin derived from equine liver is incorporated.

Next, this DNA fragment is inserted into pMK-2, which is a vector-plasmid for expressing a protein, to produce a plasmid for expressing apoferritin.

Then, PCR (polymerase chain reaction) is performed, using this plasmid for expressing apoferritin as the template and a single strand DNA fragment in which a desired variation is incorporated as the primer, so that the desired variation is introduced site-specifically to a desired position of the DNA encoding the amino acids of apoferritin. Thus, a plasmid including a DNA fragment of a variant apoferritin gene in which DNA in a portion encoding the first to the eighth amino acids of the apoferritin is deleted is produced. The DNA fragment of this apoferritin gene may cut out and incorporated into another vector-plasmid, if necessary.

Then, the produced plasmid is introduced into a commercially available *E. coli* (e.g., Nova Blue) and transformed, and then this *E. coli* is cultured in a large amount at 37° C. with a jar fermentor (mass culturing apparatus). The transformed *E. coli* has resistance to ampicilline, which is used as an indicator to distinguish it from *E. coli* that has not been transformed, so that the transformed *E. coli* can be screened.

In this *E. coli*, the DNA of the recombinant apoferritin incorporated in the plasmid expresses, and apoferritin in which the first to the eight amino acid residues are deleted (hereinafter, referred to as "fer-8") has been mass-produced. fer-8 is extracted and purified from the *E. coli* bacteria in the manner described later.

Next, in order to produce fer-8-Ser, PCR is performed, using the plasmid obtained in the above-described operation to which DNA encoding the amino acid sequence of fer-8 is incorporated as the template and a single strand DNA fragment encoding the amino acid sequence in which the $128^{th}$ amino acid of aspartic acid and the $131^{st}$ amino acid of glutamic acid of apoferritin are substituted with serine as the primer.

Then, a plasmid to which DNA encoding the amino acid sequence of fer-8-Ser is inserted is produced in the same manner as for production of fer-8, and this plasmid is introduced into *E. coli* (Nova Blue) and transformed, and then the transformed *E. coli* is cultured in a large amount, and then fer-8-Ser is extracted and purified from the *E. coli* bacteria in the manner described later.

Then, a plasmid to which DNA encoding the amino acid sequence of fer-8-Ser-Arg is inserted and fer-8-Ser-Arg are obtained, and then a plasmid to which DNA encoding the amino acid sequence of fer-8-Ser-Arg-Cys is inserted and fer-8-Ser-Arg-Cys are obtained in the same manner as above.

The procedure for extracting and purifying the variant apoferritin in the above operations is as follows.

First, a culture liquid of *E. coli* that has been cultured is transferred to a centrifugal tube, set in a centrifugal separator, and centrifuged at 4° C. and 10,000 rpm for 25 min to precipitate the *E. coli* bacteria.

Next, after the precipitated bacteria are collected, the bacteria are disintegrated in a liquid with an ultrasonic disintegrator so that apoferritin is eluted in the liquid. Then, the liquid in which the bacteria are disintegrated is transferred to a centrifugal tube, set in a centrifugal separator, and centrifuged at 4° C. and 10,000 rpm for 25 min to precipitate the bacteria that has been left undisintegrated.

Next, a supernatant is collected from the centrifugal tube, and the supernatant is subjected to a heat treatment at 60° C. for 15 min, and then transferred to a centrifugal tube for centrifugation at 4° C. and 10,000 rpm for 25 min. This operation modifies unwanted protein, which precipitates in the bottom of the tube.

Then, after a supernatant is collected from the centrifugal tube, column chromatography is performed with Q-sepharose HP (gel filtration column) at 4° C. to collect an apoferritin fraction contained in the supernatant. This apoferritin fraction is further passed through Sephacryl S-300 (gel filtration column) at 25° C. for column chromatography so as to be purified. This operation removes impurities and a purified recombinant apoferritin can be obtained.

In the present invention, when DNA encoding a modified apoferritin can be obtained, this DNA can be amplified by a known technique. Therefore, for mass production of recombinant apoferritin, there is no need to perform a process of recombination of genes again.

Production of Apoferritin Holding Gold Particles

First, a recombinant apoferritin solution and a $KAuCl_4$ solution (or $HAuCl_4$) solution are mixed to prepare a solution in which the final concentrations of the recombinant apoferritin and $KAuCl_4$ are 0.5 mg/mL and 3 mmol/L, respectively and the pH is 7 to 9. Thereafter, the solution is allowed to stand at room temperature for at least 24 hours so that gold particles are captured into the inside of the apoferritin to form a gold-apoferritin complex. As a buffer, when the pH is 7 to 8, 100 mM phosphoric acid is preferably used, and when the pH is 8 to 9, Tris-HCl is preferably used At this point, if either one of adding $NaBH_4$ to the solution such that the concentration thereof is 1 mM or less, adding alcohol such as ethanol to the solution such that the concentration thereof is 10% or less (v/v), or irradiating the solution with light or UV rays, it is possible to accelerate the reduction reaction of $(AuCl_4)^-$ so that the reaction time can be shortened. However, if the concentration of $NaBH_4$ is more than 1 mM, or if the concentration of ethanol is more than 10% (v/v), $(AuCl_4)^-$ is reduced before being captured into the inside of the apoferritin, so that gold particles may be precipitated on the outer surface of the apoferritin. The size of the gold particles precipitated on the outer surface of the apoferritin is non-uniform to a larger extent than the size of gold particles formed in the holding portion 4 of the apoferritin.

Inside the apoferritin, the surface of the precipitated gold particles itself catalyzes the reduction reaction of $(AuCl_4)^-$ (autocatalytic function). Thus, the reduction reaction of $(AuCl_4)^-$ continues until the holding portion 4 of the apoferritin is filled.

The pH of the solution is set to 7 to 9 for the following reasons. If the pH is 6 or less, the reduction of $(AuCl_4)^-$ hardly occurs, and if the pH is 10 or more, the progress of the reduction of $(AuCl_4)^-$ cannot be controlled.

Thereafter, side reaction products and apoferritin that does not hold gold particles are removed in the same manner as when purifying ferritin including iron inside, and the resultant solution is fractionated by gel column chromatography so that the apoferritin including gold particle inside is collected in the form of a solution. In this case, apoferritin in which gold particles are formed, not in the holding portion 4, but on its outer surface and a small amount of apoferritin in which gold particles are formed both in the holding portion 4 and on the outer surface can be obtained at the same time.

If fer-8-Ser and fer-8-Arg are used as recombinant apoferritin in a reaction to capture gold particles into apoferritin, apoferritin in which gold particles are formed on its outer surface is also generated as well as apoferritin including gold particles inside. This seems to be because the speed of a reaction to precipitate gold on the outer surface of apoferritin is faster than that of a reaction to form gold particles in the holding portion 4 of the apoferritin.

On the other hand, if fer-8-Ser-Arg is used as a recombinant apoferritin, the yield of the apoferritin including gold particles inside is improved significantly. This is because the reduction reaction of $(AuCl_4)^-$ in the holding portion 4 of the apoferritin is accelerated by the reductive function of cysteine (Cys) introduced into the holding portion 4. The diameter of gold particles included inside the apoferritin is uniformly about 6 nm. In other words, gold particles having a uniform size of the nanometer order can be formed efficiently by using a recombinant apoferritin produced in this embodiment, fer-8-Ser-Arg-Cys. Fine gold particles have applications or advantages that other metals do not have, such as an application to a DNA sensor.

In this embodiment, the apoferritin derived from equine liver is used, but apoferritin derived from other organs or other living organisms, that is, proteins made of monomer subunit polymer and including a holding portion inside can be used. Apoferritin derived from some other living organisms such as Listeria ferritin derived from Listeria monocytogenes have a stereostructure similar to that of the apoferritin derived from equine, so that a recombinant apoferritin can be obtained in the same operation. The diameter of the core of a metal-apoferritin complex is slightly different, depending on the type, so that the diameter of gold particles can have a variation. In addition to that, a cage-like protein, which can hold a metal or the like inside can hold gold particles by changing the charge of the channel and the inside as done in this embodiment.

Furthermore, in the case of proteins of other ferritin families such as a Dps protein constituted with 12 monomer subunits and including an inorganic substance inside, precious metal particles can be held with the same gene recombination technique as in the case of apoferritin.

In this embodiment, the $128^{th}$ amino acid of aspartic acid and the $131^{st}$ amino acid of glutamic acid present on the inner surface of the channel 3 of apoferritin are both substituted with serine. However, instead of serine, they can be substituted with glycine or alanine, which is a neutral amino acid having an even smaller molecular weight.

In this embodiment, fer-8-Ser-Arg is used as a recombinant apoferritin, but basic, or non-polar or neutral amino acids having no negative changes, such as lysine or alanine, can be used to substitute the $58^{th}$, $61^{st}$, and $64^{th}$ amino acids of glutamic acids in the amino acid sequence of the apoferritin. A recombinant apoferritin in which the $58^{th}$, $61^{st}$, and $64^{th}$ amino acids of glutamic acids in the amino acid sequence are substituted with lysine is represented by fer-8-Ser-Lys in the following.

A recombinant apoferritin in which the $58^{th}$, $61^{st}$, and $64^{th}$ amino acids of glutamic acids in the amino acid sequence are substituted with alanine is represented by fer-8-Ser-Ala.

A recombinant apoferritin in which the $54^{th}$ amino acid of glutamic acid and the $65^{th}$ amino acid of arginine in fer-8-Ser-Lys are both substituted with cysteine is represented by fer-8-Ser-Lys-Cys. A recombinant apoferritin in which the $54^{th}$ amino acid of glutamic acid and the $65^{th}$ amino acid of arginine in fer-8-Ser-Ala are both substituted with cysteine is represented by fer-8-Ser-Ala-Cys.

Among these, the DNA sequence encoding the amino acid sequence of fer-8-Ser-Lys-Cys is described in sequence 1, and the amino acid sequence of fer-8-Ser-Lys-Cys is described in sequence 2 in the sequence listing. The amino acid of sequence 2 starts with the $9^{th}$ amino acid, tyrosine.

In fer-8-Ser-Lys-Cys produced in this embodiment, the DNA sequence encoding Lys of the $58^{th}$, $61^{st}$ and $64^{th}$ amino acids ($50^{th}$, $53^{rd}$, and $56^{th}$ amino acids in the sequence 2) of Lys are "aag", but this can be "aaa" encoding Lys, instead. For Ser of the $128^{th}$ and $131^{st}$ amino acids ($120^{th}$ and $123^{rd}$ amino acids in the sequence 2) or Cys of the $54^{th}$ and $65^{th}$ amino acids ($46^{th}$ and $57^{th}$ amino acids in the sequence 2), other sequences than those shown in the sequence 1 can be used, as long as it is a DNA sequence encoding these amino acids. This is true for other recombinant apoferritin.

The $127^{th}$ amino acid of cysteine of the recombinant apoferritin produced in this embodiment such as fer-8-Ser-Arg-Cys, fer-8-Ser-Lys-Cys and fer-8-Ser-Ala-Cys is positioned on the outer surface of the apoferritin, and it is estimated that this cysteine precipitates gold particles on the outer surface of the apoferritin. Therefore, when the $127^{th}$ amino acid of cysteine of fer-8-Ser-Arg-Cys, fer-8-Ser-Lys-Cys and fer-8-Ser-Ala-Cys is substituted with a substance having a smaller reduction function than that of the cysteine, gold particles are suppressed from being precipitated on the outer surface of the apoferritin, and the yield of the apoferritin including gold particles inside can be improved further. In order to achieve this, the $127^{th}$ amino acid of cysteine may be substituted with an amino acid such as alanine, or may be reacted with chemicals that react with a cysteine reside to suppress the reduction function.

In this embodiment, a gold-apoferritin complex is produced, but instead of introducing $(AuCl_4)^-$ to apoferritin, chloroplatinic acid $(PtCl_4)^{2-}$ is introduced into a recombinant apoferritin to produce apoferritin holding platinum particles. However, since $(PtCl_4)^{2-}$ is easily reduced in a solution of pH 7 to 9 so that platinum is precipitated in the solution, it is necessary that the pH of the solution is lower than 7. In this case, 100 mM acetic acid is used as a buffer when pH is about 4, and 100 mM β-alanine is used when pH is about 3.

An example of industrial application of the recombinant apoferritin holding precious metal produced in this embodiment will be described in the following embodiment.

Second Embodiment

Figure 5:
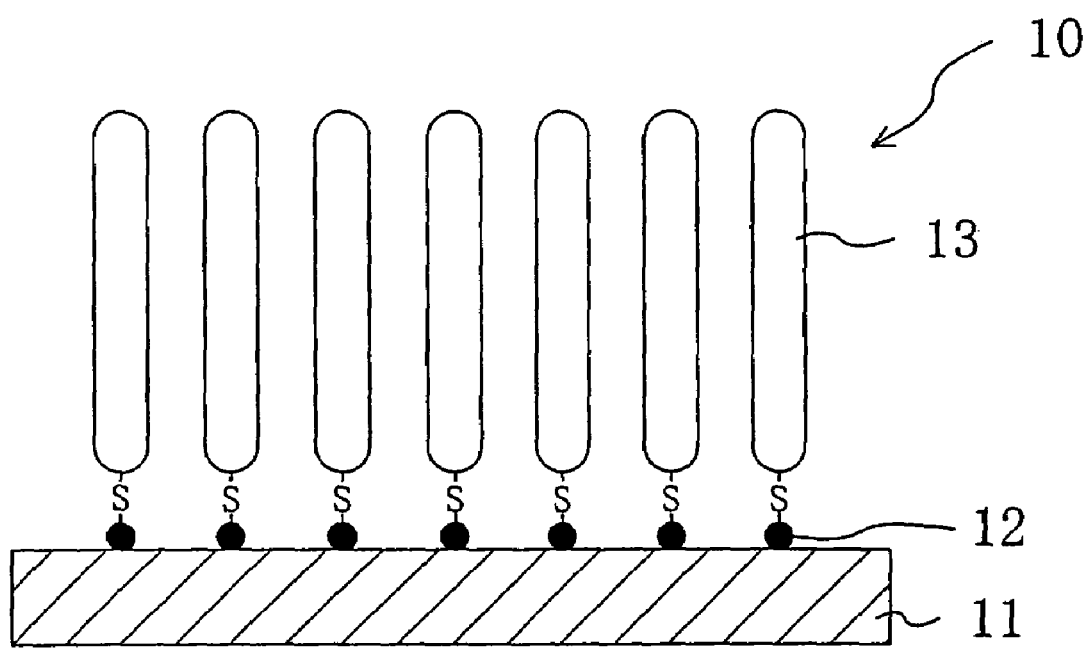
FIG. 5 is a schematic view showing a nucleotide detector according to a second embodiment of the present invention.

First, the structure of the nucleotide detector in this embodiment will be described. FIG. 5 is a cross-sectional view showing the structure of the nucleotide detector in this embodiment.

As shown in FIG. 5, the nucleotide detector 10 in this embodiment is a DNA sensor, and includes a substrate 11, gold particles 12 having a nanometer size (a diameter of about 6 nm) arranged on the surface of the substrate 11 with high density and high precision (with a gap of about 12 nm between neighboring particles), and single stranded DNAs (thiol DNAs) 13 having a sulfur atom at their ends, and the gold particles 12 are bonded to the thiol DNAs 13.

Next, a method for producing the nucleotide detector 10 in this embodiment will be described. In order to produce the nucleotide detector 10 in this embodiment, the gold particles 12 having a diameter of about 6 nm should be arranged and fixed two-dimensionally with high density and high precision on the surface of the substrate 11.

First, the recombinant apoferritin holding the gold particles 12 of the first embodiment (a complex of fer-8-Ser-Arg-Cys and gold particles; referred to as gold-including apoferritin 15 in the following) are arranged on the surface of the substrate 11 in a method as described below.

Figure 3:
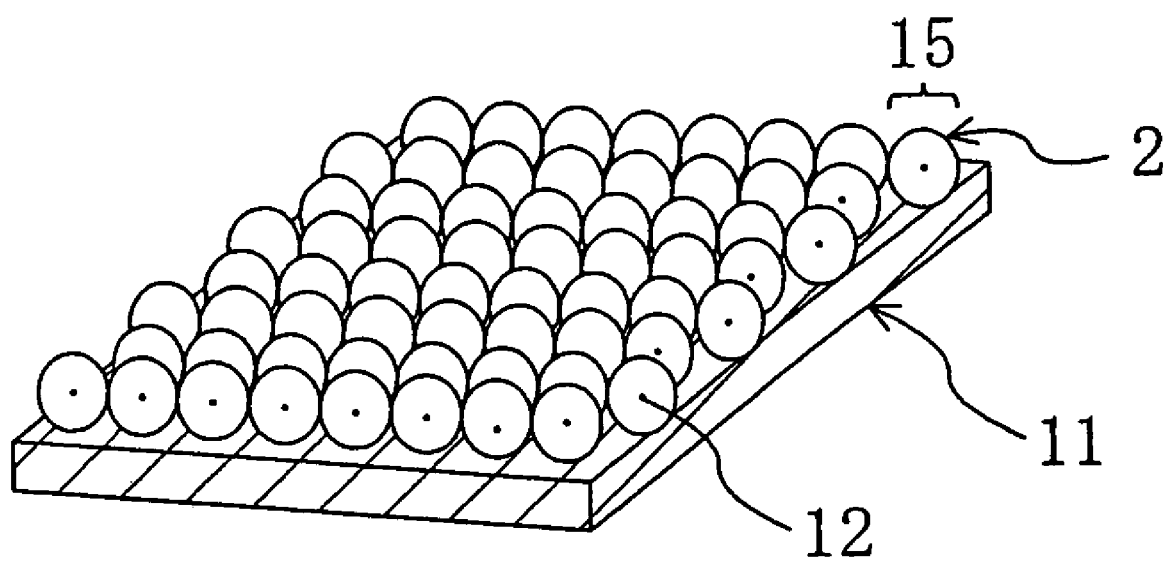
FIG. 3 is a schematic view of gold-including apoferritin arranged on a substrate.
Figure 4:
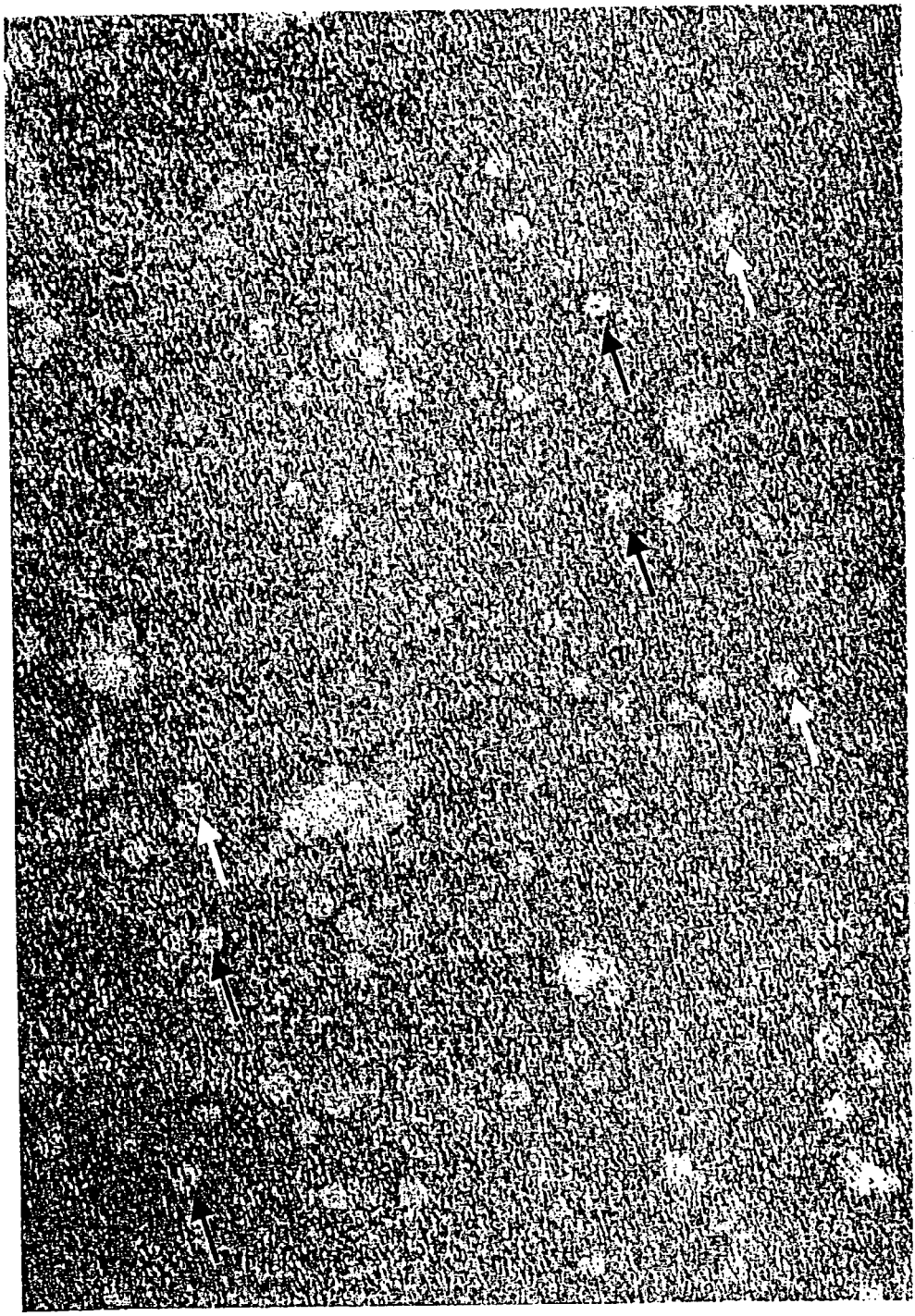
FIG. 4 is an electron micrograph of the gold-including apoferritin arranged on a substrate.

FIG. 3 is a schematic view showing the gold-including apoferritin 15 arranged on the substrate 11, and FIG. 4 is an electron micrograph of the gold-including apoferritin 15 arranged on the substrate 11.

For imaging of the electron micrograph of FIG. 4, gold glucose having a size that is large enough not to be captured into apoferritin is used for staining. Gold glucose staining is used because when staining is performed with a regular pigment, the pigment enters the apoferritin so that the presence of a gold particle cannot be confirmed.

This operation forms a film of the gold-including apoferritin 15 arranged with high density and high precision as shown in FIG. 3 on the substrate 11. FIG. 4 indicates that the outer diameter of the apoferritin is about 12 nm.

Then, the outer shell 2 made of protein of the gold-including apoferritin 15 is removed so that only the gold particles 12 are left. Then, the thiol DNAs 13 are bonded to the gold particles 12. The DNAs used here are single stranded DNAs.

In this embodiment, a known method can be used to arrange and fix the gold-including apoferritin 15 two-dimensionally with high density and high precision on the surface of the substrate 11.

For example, the transfer method (Adv. Biophys., Vol. 34, p 99–107 (1997)) that has been developed by Yoshimura et al, which will be described below, can be used.

In this method, first, a liquid in which the gold-including apoferritin 15 is dispersed is injected to a 2% sucrose solution with a syringe. Then, the liquid comes up toward the liquid surface of the sucrose solution.

Then, the liquid that has first reached the interface between air and the liquid forms an amorphous film made of modified apoferritin, and the liquid that has reached later is attached under the amorphous film.

Then, two-dimensional crystal of the gold-including apoferritin 15 is formed under the amorphous film. Then, the substrate 11 (silicon wafer, carbon grid, glass substrate or the like) is placed on the film consisting of the amorphous film and the two-dimensional crystal of the gold-including apoferritin 15, so that the film including the gold-including apoferritin 15 is transferred onto the surface of the substrate 11.

This method makes it possible to arrange the gold-including apoferritin 15 on the substrate 11 with high density and high precision, as shown in FIG. 3.

In this case, if the surface of the substrate 11 is treated so as to be hydrophobic, the film can be transferred onto the surface of the substrate 11 more easily.

Next, the outer shell 2 made of protein is removed. Protein molecules are generally weak to heat, so that the outer shell 2 can be removed by a heat treatment as described below.

For example, when the substrate 11 with the gold-including apoferritin 15 is left undisturbed in an inert gas such as nitrogen at 400 to 500° C. for about one hour, the outer shell 2 and the amorphous film made of protein are burned out, so that the gold particles 12 remain on the substrate 11 in the form of dots that are arranged regularly in a two-dimension with high density and high precision.

As described above, the gold particles 12 held in the gold-including apoferritin 15 are allowed to appear on the substrate 11 two-dimensionally and arranged with high density and high precision.

Next, formation of the nucleotide detector 10 of this embodiment will be described below.

The nucleotide detector 10 of this embodiment is obtained by bonding thiol DNAs 13 to the gold particles 12 arranged on the substrate 11 in the manner as described above.

The gold particles 12 can be bonded to the thiol DNAs 13 simply by bringing the substrate 11 in which the gold particles 12 are arranged into contact with an aqueous solution of the thiol DNAs 13 and leaving as it is for a predetermined time. This bonding can be achieved because sulfur easily reacts with gold and thus easily forms a covalent bond with the gold particles 12 at the end of the thiol DNA 13 or thiol RNA.

More specifically, when the thiol DNAs 13 in the aqueous solution are brought into contact with the gold particles 12 on the substrate 11, sulfur atoms S of the thiol DNAs 13 are covalently bonded to the gold particles 12 in the one-to-one correspondence manner, so that the thiol DNAs 13 are arranged on the substrate 11 with very high density and high precision. Since the gold particles 12 on the substrate 11 are arranged two-dimensionally with very high density and high precision, the thiol DNAs 13 bonded to the gold particles 12 are also arranged two-dimensionally with high density and high precision, so that in the nucleotide detector 10, particles are arranged uniformly in the number per unit in accordance with the size of the particles.

In this process, instead of the thiol DNAs 13, thiol RNAs or nucleotides such as PCR primer whose end is thiolized can be used.

In the above process, the concentration of the thiol DNAs 13 in the aqueous solution can be theoretically such that the number of the gold particles 12 on the substrate 11 matches the number of thiol DNAs 13. However, in reality, it is preferable that the number of the thiol DNAs 13 is larger than that of gold particles 12. Therefore, in this embodiment, an aqueous solution including a high concentration of the thiol DNAs 13 is used so that the thiol DNAs 13 are contained in the number of molecules of more than that of the gold-including apoferritin 15 that is contained in the liquid in the form of a dispersion.

Furthermore, as the temperature of the aqueous solution of the thiol DNAs 13 is higher, the bonding between the sulfur atoms S of the thiol DNAs 13 and the gold particles 12 is promoted. However, if the temperature is too high, it becomes difficult to handle the thiol DNAs 13, for example, due to a large convection current. Furthermore, too high temperatures are also disadvantageous in view of energy consumption, so that in general, it is preferable to heat the aqueous solution of the thiol DNAs 13 to about 20 to 60° C. for the above-described process.

Thus, the nucleotide detector 10 of this embodiment that is capable of easily detecting DNA or RNA to be detected can be obtained.

Next, a method for detecting DNA when the nucleotide detector 10 is used as a DNA sensor will be described.

First, a solution containing a DNA group to be subjected to detection (DNA group to be detected) is prepared and the DNA group to be detected has been subjected to a fluorescent-labeling treatment beforehand.

The solution of the fluorescent-labeled DNA group to be detected is brought into contact with the nucleotide detector 10 in which the thiol DNAs 13 are arranged and left undisturbed.

After a predetermine period of time has passed, when there is a DNA hybridized with the thiol DNA 13 of the nucleotide detector 10 in a group of DNAs to be detected, the thiol DNA 13 of the nucleotide detector 10 and the DNA in the group of DNAs to be detected constitute a double helix and establish a stable bond.

Next, if the nucleotide detector 10 is washed with a solution free from a phosphor, such as water, the DNA that is not bonded to the thiol DNA 13 of the nucleotide detector 10 in the group of DNAs to be detected and a trace amount of phosphors left on the nucleotide detector 10 can be removed.

Thereafter, fluorescence is observed by irradiating the surface of the nucleotide detector 10 with a light source such as laser. At this point, if there is a DNA having a sequence that is hybridized with the thiol DNA 13 of the nucleotide detector 10 in the group of DNAs to be detected, fluorescence occurs.

As described above, whether or not there is a DNA having a predetermined sequence in the group of DNAs to be detected can be detected by detecting whether or not fluorescence occurs.

In particular, in the nucleotide detector 10 of this embodiment, the thiol DNAs are arranged with high density and high precision uniformly over the entire substrate. Therefore, the intensity of fluorescence is high, and the fluorescence occurs highly precisely and uniformly, so the nucleotide detector 10 of this embodiment can be used as a high performance DNA sensor having a very high SN ratio. Therefore, when the nucleotide detector 10 of this embodiment is used as a DNA sensor and a fluorescence intensity higher than a predetermined value is obtained, it is determined that a DNA having a predetermined sequence is present in the group of DNAs to be detected. That is to say, there is almost no possibility of erring in the determination of the presence of the DNA having a predetermined sequence.

Furthermore, in the nucleotide detector 10 of this embodiment, the thiol DNAs are arranged with high density and high precision uniformly over the entire substrate, and there is almost no possibility that the fluorescence intensity after the hybridization of the DNA having a predetermined sequence differs from substrate to substrate. Therefore, there is no need of changing the setting of a threshold of the fluorescence intensity for each substrate in order to determine the presence of hybridized DNAs, which reduces the time and labor of the adjustment of a fluorescence detector.

In this embodiment, the case where the nucleotide detector 10 is used as a DNA sensor has been described. However, the nucleotide detector 10 is used as a RNA sensor by using a group of RNAs, instead of the group of DNAs to be detected.

Furthermore, conventional nucleotide detectors such as DNA chips have to be disposed of, but in the nucleotide detector 10 of this embodiment, the substrate and the DNA (or RNA) is fixed firmly via a sulfur atom and a gold particle, so that this fixture can be maintained even at a temperature of 100° C. Therefore, the nucleotide detector 10 can be used repeatedly by dissociating the hybridized DNA from the thiol DNA and washing it away.

Furthermore, a gold-apoferritin complex in which gold particles are grown on its outer surface that is obtained in the first embodiment may be used, instead of the gold-including apoferritin 15 used in this embodiment. Although the sizes of the gold particles that are grown on the outer surface of apoferritin are not uniform, but similarly to the gold particles 12 used in this embodiment, the gold particles can be arranged on a substrate with high density and high precision. In the first embodiment, when fer-8-Ser-Arg is used, fer-8-Ser-Arg in which gold particles are grown on the outer surface with very high yield can be obtained, so that compared to the case where the gold-including apoferritin 15 is used, the production cost of the nucleotide detector 10 can be reduced.

Third Embodiment

In this embodiment, a nonvolatile memory cell including dot bodies formed by utilizing the gold-including apoferritin produced in the first Embodiment for a floating gate will be described. It should be noted that the nonvolatile memory cell in this embodiment and the method for producing the same are those described in Japanese Laid-Open Patent Publication No. 11-233752.

Figure 6:
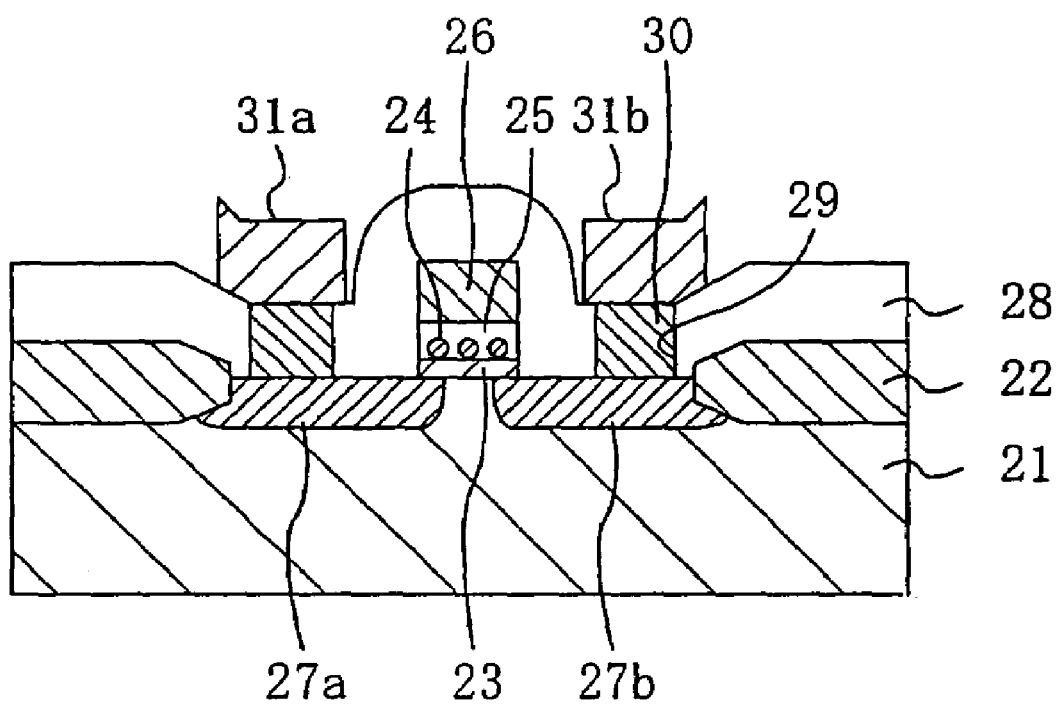
FIG. 6 is a cross-sectional view showing the structure of a non-volatile memory cell in which dot bodies made of gold particles are used for a floating gate according to a third embodiment of the present invention.

FIG. 6 is a cross-sectional view showing the structure of the nonvolatile memory cell utilizing dot bodies for a floating gate. As shown in FIG. 6, on a p-type Si substrate 21, a polysilicon electrode 26 that functions as a control gate, dot bodies 24 that are made of gold fine particles having a particle size of about 6 nm and functions as a floating gate electrode, a gate oxide film 23 that is present between the p-type Si substrate 21 and the floating gate and functions as a tunnel insulating film, a silicon oxide film 25 that is present between the control gate and the floating gate and functions as an interelectrode insulating film for transmitting a voltage of the control gate to the floating gate are provided. In the p-type Si substrate 21, first and second n-type diffusion layers 27a and 27b that function as a source or a drain are formed, and a region between the first and second n-type diffusion layers 27a and 27b in the p-type Si substrate 21 functions as a channel. Furthermore, an element isolation oxide film 22 formed by a selection oxidation method or the like for electrical separation is formed between the memory cell shown in FIG. 6 and a memory cell adjacent thereto. The first and second n-type diffusion layer 27a and 27b are connected to first and second aluminum wiring 31a and 31b, respectively, via tungsten 30. Although not shown in FIG. 6, the polysilicon electrode 26 and the p-type Si substrate 21 are also connected to aluminum wiring, so that the voltage of each portion of the memory cell is controlled by using the aluminum wiring or the like.

This memory cell can be formed easily as follows.

First, the element isolation oxide film 22 enclosing an active region is formed by a LOCOS method, and then the gate oxide film 23 is formed on the substrate. Thereafter, the dot bodies 24 are formed over the entire substrate with the gold-including apoferritin produced in the first embodiment. By using the gold-including apoferritin in this process, the process of reducing the dot bodies, which was necessary when a conventional apoferritin including a metal oxide was used, can be omitted.

Next, a silicon oxide film and a polysilicon film to bury the dot bodies 24 are deposited on the substrate by a CVD method.

Next, the silicon oxide film and the polysilicon film are patterned so that the silicon oxide film 25 that serves as an interelectrode insulating film and the polysilicon electrode 26 that serves as a control gate electrode are formed. Thereafter, impurity ions are implanted, using a photoresist mask and the polysilicon electrode 26 as a mask, so that the first and second n-type diffusion layer 27a and 27b are formed.

Then, using known methods, an interlayer insulating film 28 is formed, contact holes 29 are opened in the interlayer insulating film 28, tungsten plugs 30 are formed by filling the contact holes 29 with tungsten, and the first and second aluminum wiring 31a and 31b are formed.

The memory cell of this embodiment is provided with a MOS transistor (memory transistor) including the polysilicon electrode 26 that functions as the control gate, the first and second n-type diffusion layers 27a and 27b that function as the source or the drain, and this memory cell is a nonvolatile memory cell that utilizes that fact that the threshold voltage of the memory transistor is changed with the amount of charges accumulated in the dot bodies 24 that function as the floating gate. This nonvolatile memory cell can be provided with the function as a memory storing binary values, but a multivalued memory storing three or more values can be realized by not only depending on the presence of charges accumulated in the dot bodies 24, but also controlling the amount of the accumulated charges.

To erase data, FN (Fowler-Nordhein) current via an oxide film or direct tunneling current can be utilized.

To write data, FN (Fowler-Nordhein) current via an oxide film, direct tunneling current or channel hot electron (CHE) implantation can be utilized.

According to the nonvolatile memory cell of this embodiment, the floating gate is made of gold fine particles having a small particle size so as to function as a quantum dot, so that the amount of the accumulated charge is small. Therefore, the amount of current for write and erase can be small, so that a nonvolatile memory cell having a low power consumption can be produced.

Furthermore, in the nonvolatile memory cell of this embodiment, since the sizes of the gold fine particles constituting the floating gate are uniform, the characteristics at the time of implantation and removal of charges are uniform among the gold fine particles, so that control can be performed easily in these operations.

Furthermore, the dot bodies 24 may be formed continuously while being in contact with each other, that is, may be formed so as to constitute a film as a whole, or may be formed discretely so that they are apart from each other. In this embodiment, since the apoferritin including gold fine particles is used, such a fine dot body pattern can be formed easily by subjecting a desired portion of the substrate to a treatment that let the portion hydrophobic, and then arranging the apoferritin or other methods.

In this embodiment, gold is used as the material of the dot bodies, but instead of this, platinum can be used. Dot bodies made of platinum having a uniform diameter of about 6 nm can be formed by using platinum-including apoferritin produced in the first embodiment, instead of the gold-including apoferritin. In this case as well, it is advantageous that the process of reducing the dot bodies is not necessary similarly to the case where the gold-including apoferritin is used.

Fourth Embodiment

In this embodiment, a method for arranging gold particles on a substrate, utilizing the gold-including apoferritin of the first embodiment, and using these gold particles as an etching mask will be described.

Figure 7:
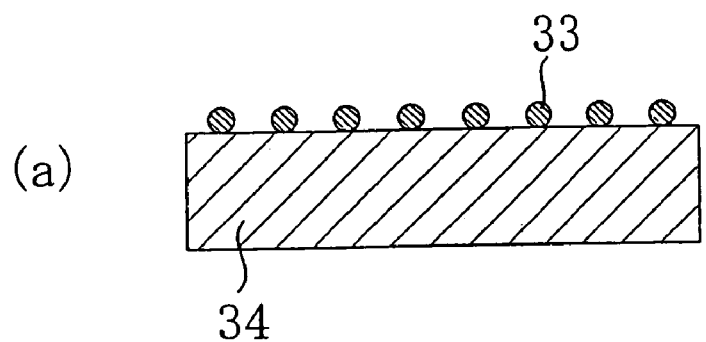
FIGS. 7a to 7c are cross-sectional views showing a process for forming a microstructure according to a fourth embodiment of the present invention.
Figure 7:
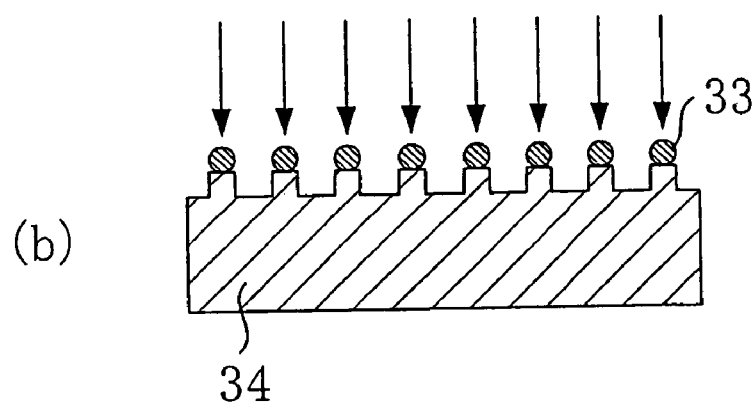
Figure 7:
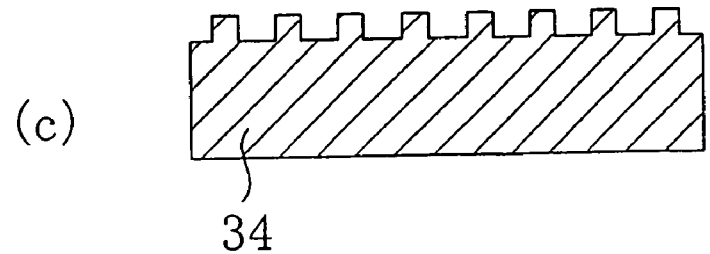

FIGS. 7A and 7C are cross-sectional views showing a method for forming microstructures using the gold particles as a mask.

First, in the process shown in FIG. 7A, the gold-including apoferritins are arranged in desired positions on a silicon substrate 34 in the same manner as in the second embodiment, and then a heat treatment is performed, so that the outer shell made of protein is removed. Thus, the gold particles 33 having a diameter of about 6 nm are left on the substrate 34.

Here, using the apoferritin including gold eliminates the reduction process that is performed when metal oxide-including apoferritin is used.

Then, in the process shown in FIG. 7B, ion reactive etching (RIE) is performed with respect to the silicon substrate 34 for 5 minutes with a $SF_6$ gas, so that the silicon substrate 34 is etched selectively. This is because the gold particles 33 are etched with more difficulty than the silicon substrate 34.

Then, in the process shown in FIG. 7C, the gold particles 33 are eventually etched when the etching proceeds further, so that the silicon substrate 34 provided with a desired pattern can be obtained. The method of this embodiment makes it possible to form uniform minute column-shaped pattern whose upper face has a diameter of about 6 nm (hereinafter, referred to as "minute column") precisely on the substrate. In other words, the method of this embodiment makes it possible to form minute structures having uniform sizes (that is, precise processing of microstructures), which was conventionally difficult.

The microstructures formed by the method of this embodiment can be used as, for example, light-emitting elements utilizing a quantum effect, which will be described later.

In this embodiment, the gold particles are used as an etching mask, but platinum particles can be used instead. For this, in the process shown in FIG. 7A, the platinum-including apoferritin of the first embodiment can be used, instead of the gold-including apoferritin.

Employing ferritin including Fe or apoferritin including Ni, Co or the like may eliminate the reduction process as well, depending on the circumstance. On the other hand, employing the precious metal-including apoferritin of this embodiment can eliminate the reduction process in any circumstances.

In the process shown in FIG. 7A of this embodiment, a heat treatment is used to remove the outer shell of the gold-including apoferritin, but instead of this, ozonolysis or chemical decomposition with cyanogen bromide (CNBr) can be used.

Fifth Embodiment

In a fifth embodiment, a method for producing an optical semiconductor device described in Japanese Laid-Open Patent Publication No. 08-083940 reported by Eriguchi et al., using the minute columns formed by the processing method of the fourth embodiment will be described below.

Figure 8:
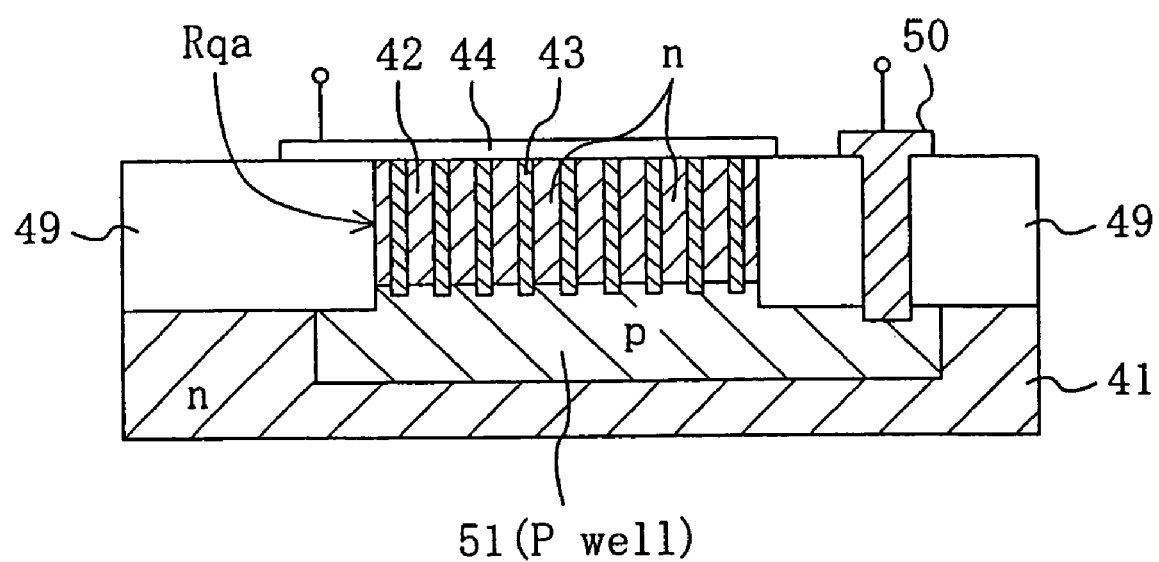
FIG. 8 is a cross-sectional view of an optical semiconductor device according to a fifth embodiment, which utilizes the microstructure formed in the fourth embodiment.

FIG. 8 is a cross-sectional view of an optical semiconductor device using semiconductor minute columns whose upper surface has a diameter of 6 nm formed in the fourth embodiment.

First, the fourth embodiment uses a substrate obtained by forming a p-type well 51 in a part of an n-type silicon, and further forming an n-type well on the p-type well 51. This substrate is processed by the method of the fourth embodiment, and semiconductor minute columns 42 made of n-type silicon are formed with high density.

Then, the side faces of the semiconductor minute columns are covered with an insulating layer 43 made of silicon oxide film by thermal oxidation, and then the gaps between the semiconductor minute columns 42 are filled with the insulating layer 43 and the end surface thereof is smoothed.

Furthermore, the insulating layer on the surface of the smoothed end portion of the semiconductor minute columns 42 of the insulating layer 43 is removed, and a transparent electrode 44 is formed.

The quantitized region Rqa on the silicon substrate 41 on the side is divided from other regions by insulating separation layers 49 that have been previously formed. In addition, a side electrode 50 penetrating the insulating separation layer 49 has been previously formed, and connected to the silicon substrate 41 that functions as a lower electrode with respect to the transparent electrode 44, which is the upper electrode of the semiconductor minute columns 42.

Thus, an optical semiconductor device is formed, and when a voltage in the forward direction is applied between the transparent electrode 44 and the side electrode 50, electroluminescence occurs at room temperature. Furthermore, visible light electroluminescence corresponding to emission of red, blue and yellow is generated by changing the carrier implantation voltage.

According to this embodiment, an optical semiconductor device having a high luminous efficiency, which was conventionally difficult to produce, can be realized.

Other Embodiments

In the process of producing the gold-apoferritin complex of the first embodiment, a small amount of gold-apoferritin complexes holding gold particles both on the outer surface and the holding portion can be obtained.

Figure 9:
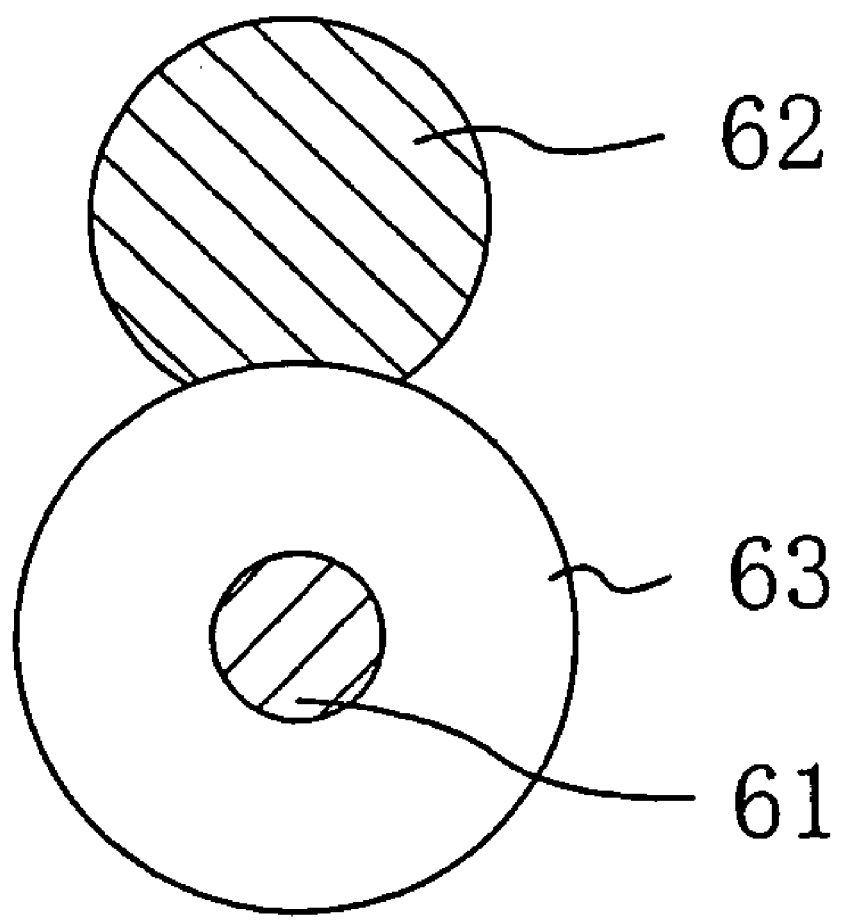
FIG. 9 is a schematic view showing a gold-apoferritin complex holding precious metal particles both on the outer surface and in the holding portion.

FIG. 9 is a view showing a gold-apoferritin complex holding gold particles both on the outer surface and the holding portion. In FIG. 9, the diameter of a first gold particle 61 held in the holding portion is about 6 nm, and the size of a second gold particle 62 formed on the outer surface of apoferritin has a variation, but it is at least true that the size is larger than the size of the first gold particle 61 included in apoferritin. The first gold particle 61 held in the holding portion is enclosed by an outer shell 63 of apoferritin.

The gold-apoferritin complexes are arranged on a silicon substrate or the like in the form of a film in such a manner that the second gold particle 62 is positioned in an upper portion.

This substrate is further processed so that a nonvolatile memory cell of a double dot type having the first gold particle 61 and the second gold particle 62 as a floating gate can be produced. This nonvolatile memory cell is characterized in that the retention time of data is long. This is because particles having different sizes are different in how easy they receive or release charges from each other, so that input information can be held in the gold particle that more hardly releases charges. Here, a nonvolatile memory cell having a long retention time can be produced easily by using the gold-apoferritin complex.

Furthermore, the apoferritin makes it possible to use gold particles having a nanometer size as a floating gate, so that a memory cell can be miniaturized.

In this embodiment, only the gold-apoferritin complex is used, but a complex of other metals and apoferritin can be used in combination with the gold-apoferritin complex, so that dots having different levels can be produced, and therefore a nonvolatile memory having a long retention time can be produced.

In this embodiment, instead of the apoferritin holding gold particles both on the outer surface and the holding portion, apoferritin holding platinum particles both on the outer surface and the holding portion can be used. Alternatively, the apoferritin holding platinum particles both on the outer surface and the holding portion can be used in combination with the apoferritin holding gold particles.

According to the recombinant apoferritin of the present invention and the method for producing the same, and the precious metal-recombinant apoferritin complex and the method for producing the same, a precious metal atom can be introduced into the apoferritin by modifying the internal structure using a gene recombination technique, and it is possible to form precious metal particles that can be applied to various microstructures. Furthermore, the recombinant apoferritin can be obtained efficiently by using the *E. coli* and the recombinant genes of the present invention.

What is claimed is:

1. A method for fabricating a precious metal-recombinant apoferritin complex, the method comprising a step of mixing the recombinant apoferritin and anionic precious metal complex ions consisiting of at least one of gold (Au) or platinum (Pt) complex ions, wherein:
   the amino acid residue of the recombinant apoferritin that corresponds to the 50$^{th}$ residue of SEQ ID NO:2 is substituted with a basic amino acid, a nonpolar amino acid, or a neutral amino acid;
   the amino acid residue of the recombinant apoferritin that corresponds to the 53$^{rd}$ residue of SEQ ID N022 is substituted with a basic amino acid, a nonpolar amino acid, or a neutral amino acid;
   the amino acid residue of the recombinant apoferritin that corresponds to the 56$^{th}$ residue of SEQ ID NO:2 is substituted with a basic amino acid, a nonpolar amino acid, or a neutral amino acid;
   the amino acid residue of the recombinant apoferritin that corresponds to the 120$^{th}$ residue of SEQ ID NO:2 is substituted with serine (Ser), alanine (Ala), or glycine (Gly);
   the amino acid residue of the recombinant apoferritin that corresponds to the 123$^{rd}$ residue of SEQ ID NO:2 is substituted with serine (Ser), alanine (Ala), or glycine (Gly);
   the recombinant apoferritin comprises a residue that corresponds to the 46$^{th}$ residue of SEQ ID NO:2; and
   the resulting complex comprises recombinant apoferritin holding a precious metal complex therein, and the precious metal complex consisting of at least one of gold (Au) or platinum (Pt).

2. The method for fabricating a precious metal-recombinant apoferritin complex according to claim 1, wherein the amino acid residue of the recombinant apoferritin that corresponds to the 50th residue of SEQ ID NO:2 is substituted with a basic amino acid.

3. The method for fabricating a precious metal-recombinant apoferritin complex according to claim 2, wherein the basic amino acid is arginine (Arg).

4. The method for fabricating a precious metal-recombinant apoferritin complex according to claim 2, wherein the basic amino acid is lysine (Lys).

5. The method for fabricating a precious metal-recombinant apoferritin complex according to claim 1, wherein the amino acid residue of the recombinant apoferritin that corresponds to the 50th residue of SEQ ID NO:2 is substituted with a nonpolar amino acid.

6. The method for fabricating a precious metal-recombinant apoferritin complex according to claim 5, wherein the nonpolar amino acid is alanine (Ala).

7. The method for fabricating a precious metal-recombinant apoferritin complex according to claim 1, wherein the amino acid residue of the recombinant apoferritin that corresponds to the 50th residue of SEQ ID NO:2 is substituted with a neutral amino acid.

8. The method for fabricating a precious metal-recombinant apoferritin complex according to claim 1, wherein the amino acid residue of the recombinant apoferritin that corresponds to the 53rd residue of SEQ ID NO:2 is substituted with a basic amino acid.

9. The method for fabricating a precious metal-recombinant apoferritin complex according to claim 8, wherein the basic amino acid is arginine (Arg).

10. The method for fabricating a precious metal-recombinant apoferritin complex according to claim 8, wherein the basic amino acid is lysine (Lys).

11. The method for fabricating a precious metal-recombinant apoferritin complex according to claim 1, wherein the amino acid residue of the recombinant apoferritin that corresponds to the 53rd residue of SEQ ID NO:2 is substituted with a nonpolar amino acid.

12. The method for fabricating a precious metal-recombinant apoferritin complex according to claim 11, wherein the nonpolar amino acid is alanine (Ala).

13. The method for fabricating a precious metal-recombinant apoferritin complex according to claim 1, wherein the amino acid residue of the recombinant apoferritin that corresponds to the 53rd residue of SEQ ID NO:2 is substituted with a neutral amino acid.

14. The method for fabricating a precious metal-recombinant apoferritin complex according to claim 1, wherein the amino acid residue of the recombinant apoferritin that corresponds to the 56th residue of SEQ ID NO:2 is substituted with a basic amino acid.

15. The method for fabricating a precious metal-recombinant apoferritin complex according to claim 14, wherein the basic amino acid is arginine (Arg).

16. The method for fabricating a precious metal-recombinant apoferritin complex according to claim 14, wherein the basic amino acid is lysine (Lys).

17. The method for fabricating a precious metal-recombinant apoferritin complex according to claim 1, wherein the amino acid residue of the recombinant apoferritin that corresponds to the 56th residue of SEQ ID NO:2 is substituted with a nonpolar amino acid.

18. The method for fabricating a precious metal-recombinant apoferritin complex according to claim 17, wherein the nonpolar amino acid is alanine (Ala).

19. The method for fabricating a precious metal-recombinant apoferritin complex according to claim 1, wherein the amino acid residue of the recombinant apoferritin that corresponds to the 56th residue of SEQ ID NO:2 is substituted with a neutral amino acid.

20. The method for fabricating a precious metal-recombinant apoferritin complex according to claim 1, wherein the amino acid residue of the recombinant apoferritin that corresponds to the 120th residue of SEQ ID NO:2 is substituted with serine (Ser).

21. The method for fabricating a precious metal-recombinant apoferritin complex according to claim 1, wherein the amino acid residue of the recombinant apoferritin that corresponds to the 123rd residue of SEQ ID NO:2 is substituted with serine (Ser).

22. The method for fabricating a precious metal-recombinant apoferritin complex according to claim 1, wherein the amino acid residue of the recombinant apoferritin that corresponds to the 46th residue of SEQ ID NO:2 is substituted with cysteine (Cys).

23. The method for fabricating a precious metal-recombinant apoferritin complex according to claim 1, wherein the precious metal complex ions comprise $(AuCl_4)^-$.

24. The method for fabricating a precious metal-recombinant apoferritin complex according to claim 1, wherein the precious metal complex ions comprise $(PtCl_4)^{2-}$.

* * * * *

UNITED STATES PATENT AND TRADEMARK OFFICE
CERTIFICATE OF CORRECTION

| | | |
|---|---|---|
| PATENT NO. | : 7,105,323 B2 | Page 1 of 1 |
| APPLICATION NO. | : 11/229240 | |
| DATED | : September 12, 2006 | |
| INVENTOR(S) | : Ichiro Yamashita | |

It is certified that error appears in the above-identified patent and that said Letters Patent is hereby corrected as shown below:

<u>Column 23</u>

Line 32, Claim 1, "SEQ ID NO22" should be -- SEQ ID NO:2 --

Signed and Sealed this

Twentieth Day of February, 2007

JON W. DUDAS
*Director of the United States Patent and Trademark Office*